(12) United States Patent
Nagai et al.

(10) Patent No.: US 12,109,512 B2
(45) Date of Patent: Oct. 8, 2024

(54) PURIFICATION METHOD

(71) Applicant: DAIKIN INDUSTRIES, LTD., Osaka (JP)

(72) Inventors: Takabumi Nagai, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 189 days.

(21) Appl. No.: 16/956,667

(22) PCT Filed: Dec. 21, 2018

(86) PCT No.: PCT/JP2018/047314
§ 371 (c)(1),
(2) Date: Jun. 22, 2020

(87) PCT Pub. No.: WO2019/124551
PCT Pub. Date: Jun. 27, 2019

(65) Prior Publication Data
US 2020/0406166 A1     Dec. 31, 2020

(30) Foreign Application Priority Data
Dec. 22, 2017    (JP) .............................. JP2017-246852

(51) Int. Cl.
*B01D 15/20*     (2006.01)
*B01D 15/42*     (2006.01)
(Continued)

(52) U.S. Cl.
CPC ........... *B01D 15/20* (2013.01); *B01D 15/424* (2013.01); *B01J 20/284* (2013.01); *C07D 209/70* (2013.01); *C01B 32/156* (2017.08); *C07B 63/00* (2013.01)

(58) Field of Classification Search
CPC ...... B01D 15/20; B01D 15/424; B01D 15/08; B01J 20/284; C07D 209/70; C01B 32/156; C07B 63/00
See application file for complete search history.

(56) References Cited

U.S. PATENT DOCUMENTS

| | | | | |
|---|---|---|---|---|
| 5,308,481 A | * | 5/1994 | Stalling ................ | B01J 20/3219 977/735 |
| 2010/0213131 A1 | * | 8/2010 | Linford .................... | B01J 13/14 156/330.9 |

(Continued)

FOREIGN PATENT DOCUMENTS

| | | | |
|---|---|---|---|
| JP | 2004026579 A | * | 1/2004 |
| JP | 2008-280323 | | 11/2008 |

(Continued)

OTHER PUBLICATIONS

A. Amari, et.al., Optimised activation of bentonite for toluene adsorption, Applied Clay Science, vol. 47, Issues 3-4, 2010, pp. 457-461, ISSN 0169-1317, https://doi.org/10.1016/j.clay.2009.11.035. (Year: 2010).*

(Continued)

*Primary Examiner* — Bradley R Spies
*Assistant Examiner* — Jeannie McDermott
(74) *Attorney, Agent, or Firm* — Wenderoth, Lind & Ponack, L.L.P.

(57) ABSTRACT

An object of the present disclosure is to provide a method for purifying the following fullerene derivative represented by formula (1) that is advantageous in production costs. The object is achieved by the method for purifying the fullerene derivative represented by formula (1)

(Continued)

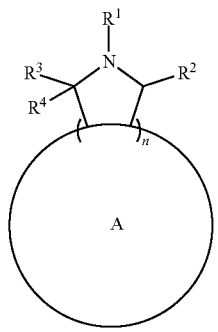

(1)

wherein
  $R^1$ represents an organic group,
  $R^2$ represents an organic group,
  $R^3$ represents a hydrogen atom or an organic group,
  $R^4$ represents a hydrogen atom or an organic group,
  ring A represents a fullerene ring,
  n represents a number of 1 or more, and
  when n is 2 or more, in one or more pairs of monocyclic moieties represented by the following partial formula:

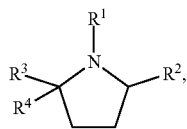

one substituent selected from the group consisting of $R^2$, $R^3$, and $R^4$ of one of the two monocyclic moieties is connected with one substituent selected from the group consisting of $R^2$, $R^3$, and $R^4$ of the other of the two monocyclic moieties to form a tricyclic moiety, the method including step 1 of contacting a composition containing the fullerene derivative represented by formula (1) as a target product for purification and one or more impure fullerene compounds with an aluminum-containing inorganic porous adsorbent.

15 Claims, 1 Drawing Sheet

(51) Int. Cl.
  *B01J 20/284* (2006.01)
  *C01B 32/156* (2017.01)
  *C07B 63/00* (2006.01)
  *C07D 209/70* (2006.01)

(56) References Cited

U.S. PATENT DOCUMENTS

| 2010/0249447 | A1* | 9/2010 | Lada ............ B82Y 40/00 977/746 |
| 2013/0306944 | A1* | 11/2013 | Kronholm ......... B82Y 30/00 252/500 |
| 2016/0093807 | A1 | 3/2016 | Nagai et al. |
| 2016/0126462 | A1 | 5/2016 | Nagai et al. |
| 2018/0282274 | A1 | 10/2018 | Nagai et al. |

FOREIGN PATENT DOCUMENTS

| JP | 2015013844 A | * | 1/2015 | |
| KR | 2017004255 A | * | 1/2017 | ............ C07C 13/64 |
| WO | 2014/185535 | | 11/2014 | |
| WO | 2014/185536 | | 11/2014 | |
| WO | 2017/061543 | | 4/2017 | |

OTHER PUBLICATIONS

Extended European Search Report issued Jul. 19, 2021 in corresponding European Patent Application No. 18892956.6, 6 pages.
International Search Report issued Jan. 29, 2019 in International (PCT) Application No. PCT/JP2018/047314.
Adsorption plant operation series, No. 7, Chemical IndustryCo., Ltd., 1975, pp. 11-15, 105-114, 121-142, cited in ISR.

* cited by examiner

PURIFICATION METHOD

TECHNICAL FIELD

The present disclosure relates to a purification method, particularly to a method for purifying a fullerene derivative.

BACKGROUND ART

Organic thin-film solar cells are formed by a coating technique using a solution of an organic compound, which is a photoelectric conversion material. The cells have various advantages: for example, 1) device production costs are low; 2) area expansion is easy; 3) the cells are more flexible than inorganic materials, such as silicon, thus having a wider range of applications; and 4) resource depletion is less likely. Thus, recent years have seen the development of organic thin-film solar cells; in particular, the use of the bulk heterojunction structure has led to a significant increase in photoelectric conversion efficiency, attracting widespread attention.

PTL 1 provides a fullerene derivative that has a specific chemical structure, and that has a purity of 99% or more based on specific elemental analysis as an excellent p-type semiconductor material among the photoelectric conversion basic materials used for organic thin-film solar cells.

PTL 2 and PTL 3 also provide other fullerene derivatives for use in organic thin-film solar cells.

CITATION LIST

Patent Literature

PTL 1: WO2014/185535A
PTL 2: WO2014/185536A
PTL 3: WO2017/061543A

SUMMARY OF INVENTION

Technical Problem

The fullerene derivative disclosed in PTL 1 that has a chemical structure represented by formula (1a):

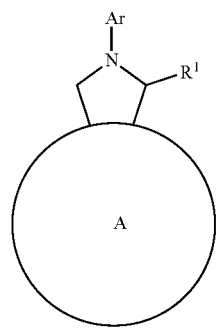

wherein ring A represents a $C_{60}$ fullerene, $R^1$ represents an alkyl group that is substituted with at least one substituent or unsubstituted or an aryl group that is substituted with at least one substituent or unsubstituted, and Ar represents an aryl group that is substituted with at least one alkyl group or unsubstituted; and that has a purity of 99% or more by specific elemental analysis, is excellent as a p-type semiconductor material. However, this compound is disadvantageous in production costs because purifying the compound after synthesis to such a high degree based on specific elemental analysis requires a substantial amount of solvent and work hours. Thus, a novel purification method that is advantageous in production costs has been in demand.

An object of the present disclosure is to provide a method for purifying a fullerene derivative represented by formula (1), which includes the chemical structure of formula (1a),

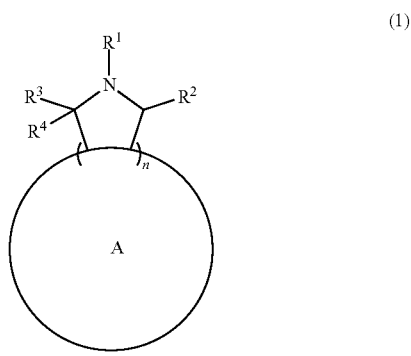

wherein
$R^1$ represents an organic group,
$R^2$ represents an organic group,
$R^3$ represents a hydrogen atom or an organic group,
$R^4$ represents a hydrogen atom or an organic group,
ring A represents a fullerene ring,
n represents a number of 1 or more, and
when n is 2 or more, in one or more pairs of monocyclic moieties represented by the following partial formula:

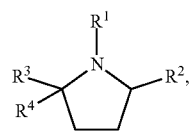

one substituent selected from the group consisting of $R^2$, $R^3$, and $R^4$ of one of the two monocyclic moieties is connected with one substituent selected from the group consisting of $R^2$, $R^3$, and $R^4$ of the other of the two monocyclic moieties to form a tricyclic moiety.

Solution to Problem

The present inventors conducted research on various purification methods, and found that the use of an aluminum-containing inorganic porous adsorbent enables purification of the fullerene derivative that has a specific chemical structure in an advantageous manner in production costs. The inventors then completed the present disclosure.

The present disclosure includes the following embodiments.

Item 1

A method for purifying a fullerene derivative represented by formula (1):

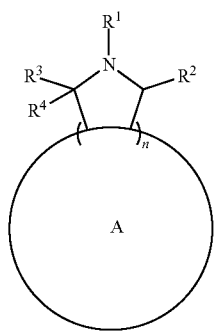

(1)

wherein
$R^1$ represents an organic group,
$R^2$ represents an organic group,
$R^3$ represents a hydrogen atom or an organic group,
$R^4$ represents a hydrogen atom or an organic group,
ring A represents a fullerene ring,
n represents a number of 1 or more, and
when n is 2 or more, in one or more pairs of monocyclic moieties represented by the following partial formula:

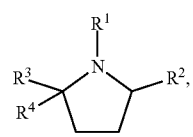

one substituent selected from the group consisting of $R^2$, $R^3$, and $R^4$ of one of the two monocyclic moieties is connected with one substituent selected from the group consisting of $R^2$, $R^3$, and $R^4$ of the other of the two monocyclic moieties to form a tricyclic moiety,
the method comprising step 1 of contacting a composition containing the fullerene derivative represented by formula (1) as a target product for purification and one or more impure fullerene compounds with an aluminum-containing inorganic porous adsorbent.

Item 2

The purification method according to claim 1, wherein $R^1$ is an aryl group that is substituted with at least one substituent or unsubstituted.

Item 3

The purification method according to claim 1, wherein ring A is a $C_{60}$ fullerene;
$R^1$ is an alkyl group that is substituted with at least one substituent or unsubstituted, or an aryl group that is substituted with at least one substituent or unsubstituted; and
$R^2$ is an aryl group that is substituted with at least one alkyl group or substituted.

Item 4

The purification method according to any one of claims 1 to 3, wherein n is 1.

Item 5

The purification method according to any one of claims 1 to 4, wherein the aluminum-containing inorganic porous adsorbent is activated clay.

Item 6

The purification method according to any one of claims 1 to 5, wherein the aluminum-containing inorganic porous adsorbent has a median size of 50 to 500 μm.

Item 7

The purification method wherein step 1 is a step of introducing the composition containing the fullerene derivative represented by formula (1), which is a target product for purification, and the one or more impure fullerene compounds into a column containing activated clay, which is a solid phase; and the method further comprises step 2 of allowing a solvent, which is a liquid phase, to flow through the column having the composition introduced to elute the fullerene derivative represented by formula (1) from the column.

Item 8

The purification method according to any one of claims 1 to 7, wherein the flow rate of the fullerene derivative represented by formula (1) per column cross-section area of 0.002 $m^2$ is 0.001 to 50 g/min.

Item 9

The purification method according to any one of claims 1 to 8, wherein the flow rate of the solvent per column cross-section area of 0.002 $m^2$ is 0.5 to 50 L/hr.

Item 10

The purification method according to any one of claims 1 to 9, wherein the amount of the solvent for use per column cross-section area of 0.002 $m^2$ is 0.5 to 100 L.

Item 11

The purification method according to any one of claims 1 to 10, wherein the ratio of the amount of the solvent used to the amount of the introduced fullerene derivative represented by formula (1) is 0.1 to 10 L/g.

Item 12

The purification method according to any one of claims 1 to 11, wherein the column has a length of 0.1 to 5 m.

Item 13

The purification method according to any one of claims 1 to 12, wherein the temperature of treatment is 0° C. to 100° C.

Advantageous Effects of Invention

The present disclosure enables purification of the fullerene derivative represented by formula (1) advantageously in production costs.

DESCRIPTION OF EMBODIMENTS

1. Terms

Figure 1:
FIG. 1 is an HPLC chart before separation and purification in Example 1.
Figure 2:
FIG. 2 is an HPLC chart after separation and purification in Example 1.

Symbols and abbreviations in the present specification can be understood as indicating the meaning typically used in the technical field to which the present disclosure pertains in accordance with the context of the specification, unless indicated otherwise.

In the present specification, the terms "content" and "purity" are interchangeably used in accordance with the context, as understood by those skilled in the art based on common technical knowledge.

In the present specification, the term "comprise" is used with the intention of including the phrase "consist essentially of" and the phrase "consist of."

Unless particularly specified otherwise, the step, treatment, or operation described in the present specification can be performed at room temperature.

In the present specification, room temperature can refer to a temperature within the range of 10 to 40° C.

In the present specification, unless particularly specified otherwise, the term "organic group" refers to a group having at least one carbon atom as its constituent atom.

In the present specification, unless particularly specified otherwise, examples of "organic group" include hydrocarbon groups.

In the present specification, unless particularly specified otherwise, the term "hydrocarbon group" refers to a group having at least one carbon atom and at least one hydrogen atom as its constituent atoms.

In the present specification, the term "hydrocarbon group" may be referred to as "hydrocarbyl group."

In the present specification, unless particularly specified otherwise, examples of "hydrocarbon group" include aliphatic hydrocarbon groups optionally substituted with at least one aromatic hydrocarbon group (e.g., benzyl group) and aromatic hydrocarbon groups optionally substituted with at least one aliphatic hydrocarbon group (aryl group).

In the present specification, unless particularly specified otherwise, the term "aliphatic hydrocarbon group" may be a linear, branched, or cyclic aliphatic hydrocarbon group, or a combination thereof.

In the present specification, unless particularly specified otherwise, the term "aliphatic hydrocarbon group" may be a saturated or unsaturated aliphatic hydrocarbon group.

In the present specification, unless particularly specified otherwise, examples of "aliphatic hydrocarbon group" include alkyl, alkenyl, alkynyl, and cycloalkyl.

In the present specification, unless particularly specified otherwise, examples of "alkyl" include a linear or branched $C_{1-10}$ alkyl, such as methyl, ethyl, propyl (e.g., propyl and isopropyl), butyl (e.g., n-butyl, isobutyl, sec-butyl, and tert-butyl), pentyl (e.g., n-pentyl, isopentyl, and neopentyl), and hexyl.

In the present specification, unless particularly specified otherwise, examples of "alkenyl" include a linear or branched $C_{2-10}$ alkenyl, such as vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In the present specification, unless particularly specified otherwise, examples of "alkynyl" include a linear or branched $C_{2-6}$ alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In the present specification, unless particularly specified otherwise, examples of "cycloalkyl" include $C_{3-8}$ cycloalkyl, such as cyclopentyl, cyclohexyl, and cycloheptyl.

In the present specification, unless particularly specified otherwise, examples of "aromatic hydrocarbon group (aryl group)" include phenyl, naphthyl, phenanthryl, anthryl, and pyrenyl.

In the present specification, unless particularly specified otherwise, examples of "alkoxy" incldue a group represented by RO— (wherein R represents alkyl).

In the present specification, unless particularly specified otherwise, the term "ester" refers to an organic group having an ester bond (i.e., —C(=O)—O— or —O—C(=O)—). Examples include groups represented by formula $RCO_2$— (wherein R represents alkyl) and groups represented by formula $R^a$—$CO_2$—$R^b$— (wherein $R^a$ represents alkyl and $R^b$ represents alkylene).

In the present specification, unless particularly specified otherwise, the term "ether group" refers to a group having an ether bond (—O—).

Examples of ether groups include polyether groups. Examples of polyether groups include groups represented by formula $R^a$—$(O—R^b)_n$— (wherein $R^a$ represents alkyl; $R^b$, in each occurrence, is identical or different and represents alkylene; and n is an integer of 1 or more). Alkylene is a divalent group formed by removing one hydrogen atom from an alkyl group.

Examples of ether also include hydrocarbyl ether groups. A hydrocarbyl ether group refers to a hydrocarbon group having at least one ether bond. A hydrocarbyl group having at least one ether bond may be a hydrocarbyl group into which at least one ether bond is inserted. Examples include a benzyl oxy group.

Examples of the hydrocarbon group having at least one ether bond include alkyl having at least one ether bond. Alkyl having at least one ether bond may be alkyl into which at least one ether bond is inserted. In the present specification, such a group may be referred to as an "alkyl ether group."

In the present specification, unless particularly specified otherwise, the term "acyl" includes alkanoyl. In the present specification, unless particularly specified otherwise, the term "alkanoyl" refers to, for example, a group represented by RCO— (wherein R represents alkyl).

In the present specification, a "5-membered heteroaryl group" refers to, for example, a 5-membered heteroaryl group containing as members of its ring at least one heteroatom (e.g., 1, 2, or 3 heteroatoms) selected from the group consisting of oxygen, sulfur, and nitrogen, unless indicated otherwise; examples of such a 5-membered heteroaryl group include pyrrolyl (e.g., 1-pyrrolyl, 2-pyrrolyl, and 3-pyrrolyl), furyl (e.g., 2-furyl, and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), and thiadiazolyl (e.g., 1,2,4-thiadiazol-3-yl and 1,2,4-thiadiazol-5-yl).

In the present specification, examples of halogen atoms include fluorine, chlorine, bromine, and iodine.

In the present specification, examples of fullerene rings include $C_{60}$ fullerenes, $C_{70}$ fullerenes, $C_{76}$ fullerenes, $C_{78}$ fullerenes, and $C_{84}$ fullerenes.

2. Purification Method

The purification method according to the present disclosure is a method for purifying the fullerene derivative represented by formula (1) (in the present specification, this fullerene derivative may be referred to as "fullerene derivative (1)"), and comprises step (1) of contacting a composition that contains fullerene derivative (1), which is a target product for purification, and one or more impure fullerene compounds, into contact with an aluminum-containing inorganic porous adsorbent.

(1) Object Treated by Purification Method

The object treated by the purification method according to the present disclosure is a composition that contains fullerene derivative (1), which is a target product for purification, and one or more impure fullerene compounds (in the present specification, this composition may be referred to as "composition (1)").

The content of fullerene derivative (1) in composition (1) to which the purification method according to the present disclosure is applied may be, for example, 40% or more, 50% or more, 60% or more, 70% or more, or 80% or more, based on the purity by HPLC analysis described below.

The content based on the purity by HPLC analysis may be, for example, 95% or less, 90% or less, or 85% or less. The content based on the purity by HPLC analysis may be, for example, 50% to 95%, 60% to 95%, or 70% to 95%.

In the present specification, "content" (or "purity") refers to the purity by HPLC analysis under the following conditions.

Conditions for HPLC Analysis

Column: COSMOSIL Buckyprep (Nacalai Tesque, Inc.) −4.5 diameter×250 mm
Solvent: toluene
Flow rate: 1 mL/min
Detection: UV-335 nm The object treated by the purification method according to the present disclosure can be a composition that contains a target product for purification, described later, and/or one or more impure substances, and that is produced from fullerenes separated and removed from the target product for purification (otherwise phrased "recovered fullerenes"), described later, as a starting material, by the purification method according to the present disclosure. The recovered fullerenes may be fullerenes recovered using substituted or unsubstituted benzenesulfonic acid (e.g., benzenesulfonic acid and ethylbenzenesulfonic acid), and may contain substituted or unsubstituted benzenesulfonic acid.

(a) Target Product for Purification

As described above, the target product for purification of the purification method according to the present disclosure is fullerene derivative (1). A preferable embodiment (embodiment 1) of fullerene derivative (1) is a fullerene derivative wherein ring A is a $C_{60}$ fullerene;
$R^2$ is Ar;
$R^2$ is an alkyl group that is substituted with at least one substituent or unsubstituted or an aryl group that is substituted with at least one substituent or unsubstituted; and
Ar is an aryl group that is substituted with at least one alkyl group or unsubstituted.

Another preferable embodiment (embodiment 2) of fullerene derivative (1) is a fullerene derivative wherein
$R^1$ is a group represented by the following formula:

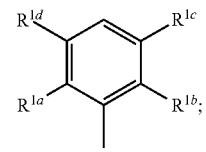

$R^{1a}$ and $R^{1b}$ are identical or different, and represent a hydrogen atom or a fluorine atom;
$R^{1c}$ and $R^{1d}$ are identical or different, and represent a hydrogen atom, a fluorine atom, an alkyl group substituted with at least one fluorine atom or unsubstituted, an alkoxy group substituted with at least one fluorine atom or unsubstituted, an ester group, or a cyano group,
$R^2$ represents
(1) a phenyl group that is substituted with at least one substituent selected from the group consisting of a fluorine atom, an alkyl group, an alkoxy group, an ester group, and a cyano group, or unsubstituted,
(2) a five-membered heteroaryl group that is substituted with 1 to 3 methyl groups or unsubstituted, or
(3) an alkyl group, an alkoxy group, an ether group, an acyl group, an ester group, or a cyano group, and
ring A represents a fullerene ring.

In this embodiment, when $R^{1a}$, $R^{1b}$, $R^{1c}$, and $R^{1d}$ are each a hydrogen atom, $R^2$ is preferably a phenyl group that is substituted with 1 or 2 fluorine atoms, or a five-membered heteroaryl group that is substituted with 1 to 3 methyl groups or unsubstituted.

In still another preferable embodiment of fullerene derivative (1) (embodiment 3),
$R^1$ is an aryl group that is substituted with at least one substituent or unsubstituted,
$R^2$ is an organic group,
$R^3$ is an organic group, and
$R^4$ is a hydrogen atom or an organic group.

In this embodiment, at least one of $R^2$ and $R^3$ is preferably an alkyl group that is substituted with at least one substituent or unsubstituted, or an alkyl ether group that is substituted with at least one substituent or unsubstituted.

$R^1$ is preferably a phenyl group that is substituted with one alkyl group or unsubstituted, and more preferably an (unsubstituted) phenyl group.

Preferably, $R^2$ can be an alkyl group that is substituted with at least one substituent selected from the group consisting of an alkoxy group, an alkoxycarbonyl group, and a polyether group, or unsubstituted. The number of substituents is preferably 1.

Preferably, $R^2$ can be an aryl group that may have at least one halogen atom (preferably fluorine). The number of substituents is preferably 0 (unsubstituted) to 2.

Preferably, $R^2$ can be a phenyl group that is substituted with 1 or 2 fluorine atoms or unsubstituted.

In a preferable embodiment of the present disclosure, the fullerene derivative represented by formula (1), which is the target product for purification, is preferably, for example, the following compounds:
formula (1B)
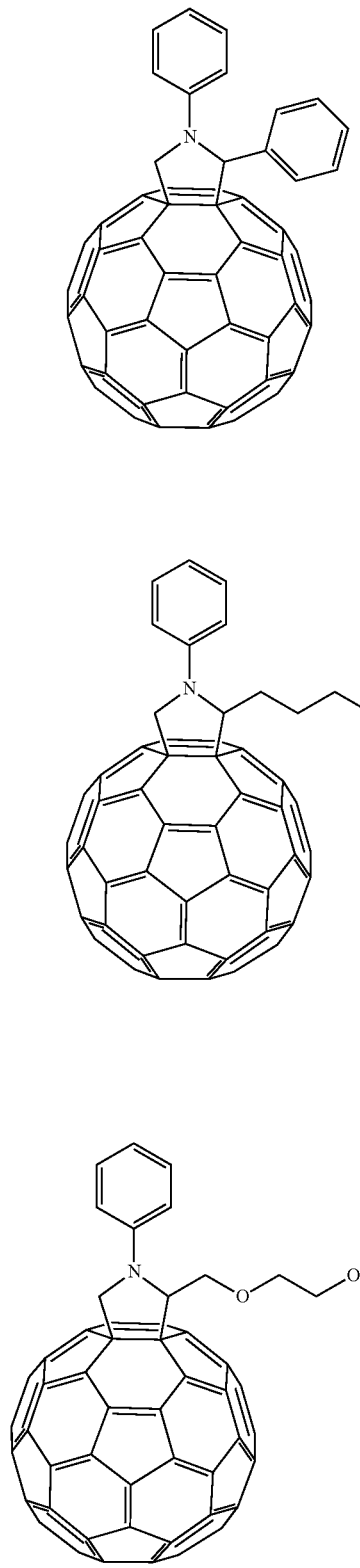
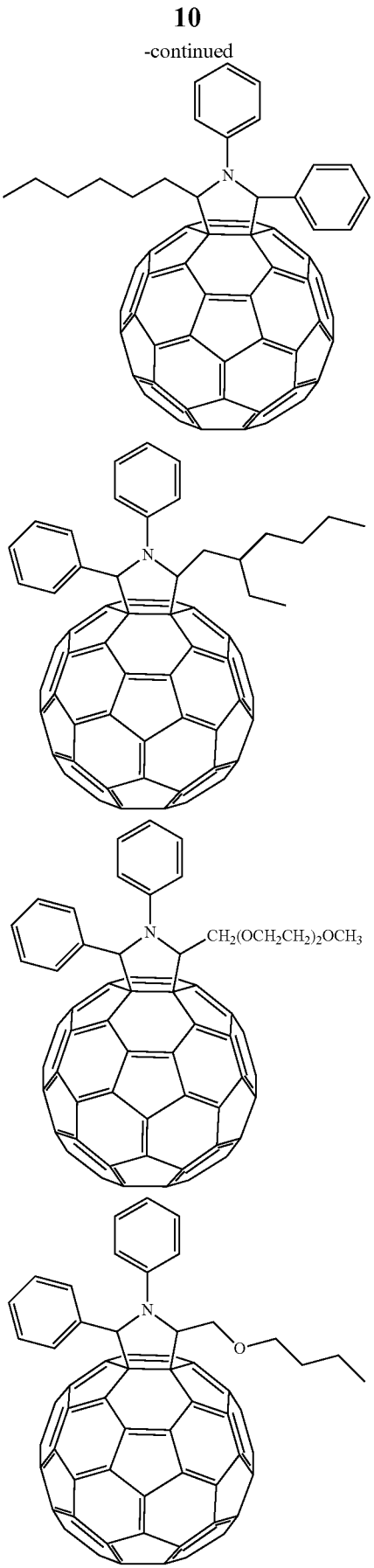

-continued

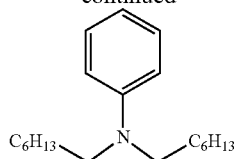
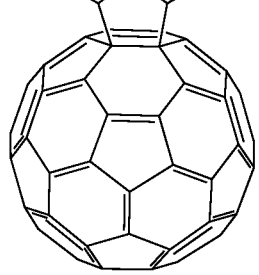
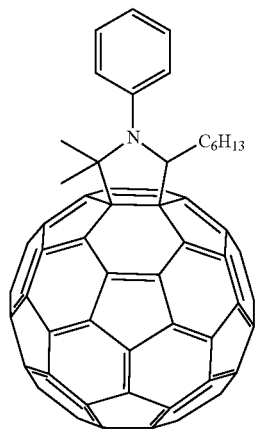
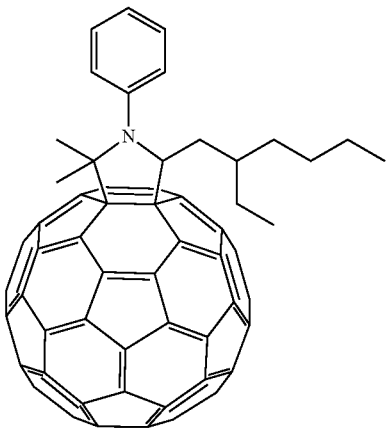
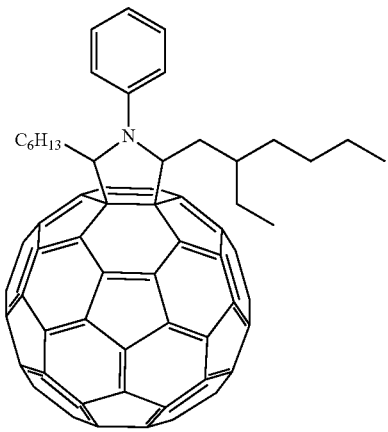

-continued

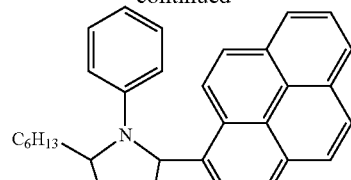
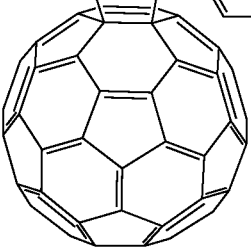

In formula (1), Ar is preferably a phenyl group that is substituted with one alkyl group or unsubstituted, and more preferably a phenyl group.

In formula (1), $R^2$ is preferably a phenyl group or an n-hexyl group.

Fullerene derivative (1) is a known compound and can be synthesized, for example, by the method disclosed in PTL 1 using the following as starting materials.

Aldehyde compound: $R^2$—CHO
N-substituted glycine: Ar—NH—CH$_2$—COOH, and
Fullerene: $C_{60}$ (The symbols in the formulas are synonymous with those in formula (1).)

Fullerene derivative (1) produced by such a method may inconveniently contain impure fullerene compounds listed as examples below.

(b) Impure Fullerene Compounds

In the present disclosure, "impure fullerene compounds" refer to fullerenes or derivatives thereof other than the target product for purification.

The impure substances may be, for example, fullerene derivatives other than fullerene derivative (1).

In an embodiment of the present disclosure in which n in formula (1) is 1 (this embodiment may be referred to as "fullerene derivative (1s)" in the present specification), typical examples of fullerene derivatives considered to be such impure substances include the following fullerene derivatives.

Impure Substance (i)
Fullerene Derivative (i)
A fullerene derivative represented by formula (i):

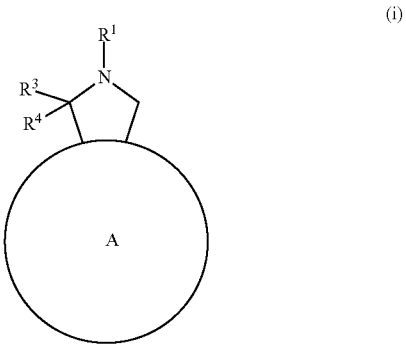

(i)

wherein
R$^1$ represents an organic group,
R$^3$ represents a hydrogen atom,
R$^4$ represents a hydrogen atom, and
ring A represents a fullerene ring.
Impure Substance (ii)
Fullerene Derivative (1m) (A Multi-adduct Product, i.e., a Polysubstituted Product)
A fullerene derivative represented by

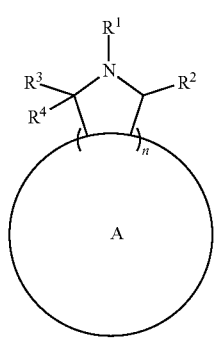

(1)

wherein
R$^1$ represents an organic group,
R$^2$ represents an organic group,
R$^3$ represents a hydrogen atom or an organic group,
R$^4$ represents a hydrogen atom or an organic group,
ring A represents a fullerene ring, and
n is a number of 2 or more (this embodiment may be referred to as "fullerene derivative (1m)" in the present specification).

These impure substances can be by-products generated during the production of fullerene derivative (1s).

As understood from this, R$^1$ and R$^2$ in formula (i) may respectively correspond to R$^1$ and R$^2$ in formula (1).
Impure Substance (iii)
Fullerene C$_{60}$
Impure Substance (iv)
An oxide of the fullerene derivative represented by formula (1), an oxide of fullerene derivative (i), an oxide of fullerene derivative (1m) (multi-adduct product), or an oxide of fullerene C$_{60}$.

This impure substance can be a starting material remaining in the production of fullerene derivative (1).

The content of fullerene derivative (1s) in composition (1) to which the purification method according to the present disclosure is applied may be, for example, 40% or more, 50% or more, 60% or more, 70% or more, or 80% or more, based on the purity by HPLC analysis described later.

In this embodiment, the content of impure substance (i) in composition (1) to which the purification method according to the present disclosure is applied may be, for example, 20% or less (e.g., within the range of 0.1 to 20%), 5% or less (e.g., within the range of 0.1 to 5%), or 0.1% or less, based on the purity by HPLC analysis described later.

In this embodiment, the content of impure substance (iim) in composition (1) to which the purification method according to the present disclosure is applied may be, for example, 50% or less (e.g., within the range of 0.1 to 50%), 10% or less (e.g., within the range of 0.1% to 10%), or 1% or less (e.g., within the range of 0.1% to 1%), based on the purity by HPLC analysis described later.

In this embodiment, the content of impure substance (iii) in composition (1) to which the purification method according to the present disclosure is applied may be, for example, 90% or less (e.g., within the range of 0.1 to 90%), 50% or less (e.g., within the range of 0.1 to 50%), or 10% or less (e.g., within the range of 0.1 to 10%), based on the purity by HPLC analysis described later.

As easily understood by a person skilled in the art, in another embodiment of the present disclosure in which fullerene derivative (1m) is the target product for purification, fullerene derivative (1s) is an impure substance. (This impure substance is referred to as "impure substance (iis).")

In this embodiment, the content of fullerene derivative (1m) in composition (1) to which the purification method according to the present disclosure is applied may be, for example, 40% or more, 50% or more, 60% or more, 70% or more, or 80% or more, based on the purity by HPLC analysis described later.

In this embodiment, the content of impure substance (i) in composition (1) to which the purification method according to the present disclosure is applied may be, for example, 20% or less (e.g., within the range of 0.1 to 20%), 5% or less (e.g., within the range of 0.1 to 5%), or 0.1% or less, based on the purity by HPLC analysis described later.

In this embodiment, the content of impure substance (iis) in composition (1) to which the purification method according to the present disclosure is applied may be, for example, 50% or less (e.g., within the range of 0.1 to 50%), 10% or less (e.g., within the range of 0.1% to 10%), or 1% or less (e.g., within the range of 0.1% to 1%), based on the purity by HPLC analysis described later.

In this embodiment, the content of impure substance (iii) in composition (1) to which the purification method according to the present disclosure is applied may be, for example, 90% or less (e.g., within the range of 0.1 to 90%), 50% or less (e.g., within the range of 0.1 to 50%), or 10% or less (e.g., within the range of 0.1 to 10%), based on the purity by HPLC analysis described later.

(2) Purification Method and Conditions for the Method (A) Aluminum-Containing Inorganic Porous Adsorbent The purification method according to the present disclosure can purify fullerene derivative (1), which is the target product for purification, using the difference in adsorption to the aluminum-containing inorganic porous adsorbent between fullerene derivative (1) and an impure fullerene compound (or the difference in elution).

In a preferable embodiment of the purification method according to the present disclosure, the purification method is performed using a column.

In the purification method in this embodiment, step 1 is a step of introducing a composition that contains the fullerene derivative represented by formula (1), which is a target product for purification, and one or more impure fullerene compounds into a column that contains an aluminum-containing inorganic porous adsorbent, which is a solid phase.

The purification method further comprises step 2 of allowing a solvent, which is a liquid phase, to flow through the column having the composition introduced to elute the fullerene derivative represented by formula (1) from the column.

The treatment of the purification method in this embodiment of the present disclosure can be performed in accordance with common technical knowledge by using a method and conditions typically used in column purification.

Examples of aluminum-containing inorganic porous adsorbents for use in the present disclosure include activated clay, bentonite, acid clay, and alumina. The aluminum-containing inorganic porous adsorbent for use in the present disclosure may be preferably a silica-alumina composite oxide. The adsorbent for use may be a single adsorbent or a combination of two or more adsorbents. Examples of preferable adsorbents include activated clay.

(i) Activated Clay, Bentonite, and Acid Clay

As is typically understood by a person skilled in the art, the "activated clay" for use in the present disclosure may be a product obtained by heat-treating acid clay with an acid. Acid clay is also clay that contains montmorillonite as the main component. Of such clay, those that are acidic are referred to as "acid clay," and those that are neutral are referred to as "montmorillonite."

The aluminum-containing inorganic porous adsorbent for use in the present disclosure (preferable example: activated clay) can preferably be in the form of particles. The particle size is preferably 0.1 to 100 μm or about 10 to 50 μm. In the present specification, the particle size of activated clay is a median size on a volume basis measured by a laser diffraction-scattering method.

The aluminum-containing inorganic porous adsorbent for use in the present disclosure (preferable example: activated clay) has a specific surface area of about 1 to about 500 $m^2/g$ or about 50 to about 350 $m^2/g$. In the present specification, the specific surface area is a value measured by the BET theory.

Aluminum-containing inorganic porous adsorbents as described above are commercially available. Examples include Activated Clay (Kishida Chemical Co., Ltd.).

(b) Flow Rate

In the purification method according to the present disclosure, the flow rate of fullerene derivative (1) per column cross-section area of 0.002 $m^2$ is preferably 0.001 to 50 g/min, preferably 0.1 to 50 g/min, more preferably 1 to 10 g/min, and still more preferably 1 to 5 g/min.

In the purification method according to the present disclosure, the ratio of the amount (volume) of the solvent used to the amount (mass) of the introduced fullerene derivative represented by formula (1) is preferably 0.1 to 10 L/g, more preferably 0.5 to 5 L/g, and still more preferably 0.5 to 2 L/g.

(c) Solvent

In the purification method according to the present disclosure, the solvent for use in elution includes:

(1) chlorine solvents, such as dichloromethane, trichloromethane (i.e., chloroform), tetrachloromethane (i.e., carbon tetrachloride), dichloroethane, and tetrachloroethane;
(2) hydrocarbon solvents, such as hexane, heptane, cyclohexane, petroleum ether, benzene, toluene, and xylene;
(3) chlorinated aromatic solvents, such as chlorobenzene and dichlorobenzene;
(4) alcohol solvents, such as ethanol and methanol;
(5) ether solvents, such as diethyl ether, diisopropyl ether, THF, DME, and dioxane;
(6) ketone solvents, such as acetone; and
(7) non-polar solvents or low-polar solvents, such as toluene, benzene, hexane, carbon disulfide, and carbon tetrachloride.

These solvents can be used singly or in a combination of two or more. Such a combination includes adding a medium-polar solvent to a low-polar solvent.

In particular, carbon disulfide, chloroform, dichloroethane, toluene, xylene, chlorobenzene, dichlorobenzene, and a combination of two or more of these substances are preferable. These substances may be used in combination with at least one member selected from the group consisting of ethanol, methanol, THF, and acetone.

When two or more solvents are used in elution, a concentration gradient may be applied to the solvents. In this case, it is preferred that the concentration of a polar solvent be gradually increased. Specifically, the following solvents and gradient conditions are preferably applied.

Preferable Examples of Solvents (Second Solvent): ethanol, methanol, THF, and acetone Concentration of Second Solvent: 0% (at the start) to 10 to 50% (at the end)

When a column is used, elution occurs in the order from a compound in which n in formula (1) is smaller through a fullerene compound in which n is larger. This provides a purified (i.e., a higher-purity) target fullerene derivative.

When a batch is used, a purified (i.e., a higher-purity)) target fullerene derivative can be obtained by washing the aluminum-containing inorganic porous adsorbent to which the fullerene derivative of formula (1) is adsorbed, by changing the solvents one by one from a solvent with a lower polarity to a solvent with a higher polarity.

The degree of polarity can be adjusted by suitably selecting solvents of different polarity, or by mixing two or more solvents of different polarity.

Solvent and Gradient Conditions

In the purification method according to the present disclosure, the flow rate of the solvent per column cross-section area of 0.002 $m^2$ is preferably 0.5 to 50 L/hr, more preferably 1 to 40 L/hr, and still more preferably 2 to 30 L/hr.

In the purification method according to the present disclosure, the amount of the solvent used per column cross-section area of 0.002 $m^2$ is preferably 0.5 to 100 L, more preferably 1 to 90 L, and still more preferably 2 to 80 L.

(d) Length of Column

In the purification method according to the present disclosure, the length of the column is preferably 0.1 to 5 m, more preferably 0.1 to 2 m, and still more preferably 0.2 to 1 m.

(e) Treatment Temperature

In the purification method according to the present disclosure, the treatment temperature is preferably 0 to 100° C., more preferably 10 to 50° C., and still more preferably 10 to 30° C.

(f) Treatment Time

In the purification method according to the present disclosure, the treatment time is preferably 0.1 to 72 hours, more preferably 0.1 to 48 hours, still more preferably 0.1 to 24 hours, even more preferably 0.1 to 10 hours, particularly preferably 0.2 to 10 hours, particularly more preferably 0.5 to 5 hours, and most preferably 1 to 2 hours.

In the purification method according to the present disclosure, the purification treatment may be performed twice or more. In this case, the method and conditions of each purification treatment may be the same or different.

3. The Effect of the Purification Method According to the Present Invention

Purity

The purification method according to the present disclosure can provide fullerene derivative (1) having a purity of preferably 95% or more, more preferably 96% or more, still more preferably 97% or more, even more preferably 98% or more, and particularly preferably 99% based on the purity by HPLC analysis.

Increase in Purity

The purification method according to the present disclosure can increase the purity of fullerene derivative (1) by preferably 15% or more, more preferably 20% or more, still more preferably 30% or more, and even more preferably 40% or more, as a difference between before and after purification, based on the purity by HPLC analysis.

A higher extent of increase is preferable. The extent of increase in purity can be, but is not limited to, for example, 50% or less, 60% or less, 70% or less, 80% or less, 90% or less, or 95% or less.

Decreases in the Content of Impure Substances

The purification method according to the present disclosure can decrease the content of impure substances by preferably 15% or more, more preferably 20% or more, still more preferably 30% or more, and even more preferably 40% or more as a difference between before and after purification based on the purity by HPLC analysis. A higher extent of decrease is preferable. The extent of decrease in the content of impure substances can be, but is not limited to, for example, 50% or less, 60% or less, 70% or less, 80% or less, 90% or less, or 95% or less.

Separation Efficiency or Recovery Percentage

In the purification method according to the present disclosure, the separation efficiency or recovery percentage of fullerene derivative (1) may be preferably 60% or more, more preferably 70% or more, still more preferably 80% or more, and even more preferably 85% or more based on the purity by HPLC analysis.

A higher separation efficiency or recovery percentage is preferable. The separation efficiency or recovery percentage of fullerene derivative (1) can be, but is not limited to, for example, 95% or less.

4. A Combination with Other Purification Methods

The purification method according to the present disclosure can be performed in combination with at least one other purification method. The purification method according to the present disclosure can be performed before and/or after at least one other purification method. The purification method according to the present disclosure can be performed preferably as a pretreatment of another purification method.

Other purification methods can be performed, for example, as follows. For example, obtained fullerene derivative (1) is purified by silica gel column chromatography (developing solvent is preferably, for example, hexane-chloroform, hexane-toluene, or hexane-carbon disulfide), and then purified by HPLC (preparative GPC) (The developing solvent is preferably, for example, chloroform, or toluene, with chloroform being particularly preferable).

Purified fullerene derivative (1) can be further purified by washing with a solvent, and recrystallization. Washing with a solvent is preferably performed by washing the solids of purified fullerene derivative (1) with a different solvent twice or more. Washing with a solvent may be performed by, for example, placing the solids of purified fullerene derivative (1) in a container, such as a recovery flask, by using a commonly used method. Washing with a solvent twice or more preferably includes washing with a solvent with a relatively high polarity (e.g., methanol and acetone) and washing with a solvent with a relatively low polarity (e.g., tetrahydrofuran (THF) and hexane). Washing with a solvent is preferably performed with a solvent with a higher polarity first in order to decrease a residual solvent. Specifically, washing with a solvent can be performed particularly preferably with methanol, acetone, dichloromethane, tetrahydrofuran (THF), and hexane in this order.

Recrystallization is performed, for example, preferably from hexane-chlorobenzene or hexane-carbon disulfide.

The use of a HPLC column for fullerene separation in combination with a purification method such as washing with a solvent and recrystallization, or the use of a HPLC column for fullerene separation as another method, may be effective in purification. A HPLC column for fullerene separation is commercially available. Examples include Cosmosil Buckyprep columns (Nacalai Tesque, Inc.). This column purification may optionally be performed twice or more.

The solvent for use in purification using an HPLC column dedicated for fullerene separation includes at least one member selected from the group consisting of toluene, chloroform and so on.

The solvents are removed from fullerene derivative (1) that has been further purified in this manner. Removal of solvents is performed preferably as follows: the supernatant solvent is removed, and then the solvents remaining in the solids of fullerene derivative (1) are removed by evaporation, followed by drying with heating (e.g., drying at 60 to 100° C. for 8 to 24 hours) under reduced pressure (e.g., 10 mmHg or less, more preferably 1 mmHg or less).

An example of other purification methods is removal of fullerenes using substituted or unsubstituted benzenesulfonic acid (e.g., benzenesulfonic acid and ethyl benzenesulfonic acid). One aspect of removal of fullerenes may be recovery of fullerenes. The recovered fullerenes can be used in producing the fullerene derivative of formula (1), and the produced fullerene derivative of formula (1) can be subjected to the purification method according to the present disclosure. Removal or recovery of fullerenes can be performed by, for example, a method in which ethyl benzenesulfonic acid is added to a liquid that contains the fullerene derivative of formula (1) and fullerenes.

EXAMPLES

Below, the present disclosure is described in more detail with reference to Examples. However, the present disclosure is not limited to the Examples.

The following describes the meaning of the symbols and abbreviations used in the Examples.

In the Examples, HPLC analysis was performed under the following conditions.

Conditions for HPLC Analysis

Column: Cosmosil Buckyprep (NACALAI TESQUE, INC.) –4.5 (diameter)×250 mm
Solvent: toluene
Flow rate: 1 mL/min
Detection: UV-335 nm In the Examples, the materials below were used.
Activated clay: Activated Clay (trade name) (Wako Pure Chemical Industries, Ltd.), Galleon Earth NFX (trade name) (Mizusawa Industrial Chemicals, Ltd.)
Celite: Celite 545 (trade name) (Kishida Chemical Co., Ltd.)
Silica gel: Silica gel 60 0.063-0.200 mm (trade name) (Merck)
Cation-exchange resin: Diaion SA 10A (trade name) (Mitsubishi Chemical Corporation)

In the Examples, the abbreviations below were used for fullerene derivatives.

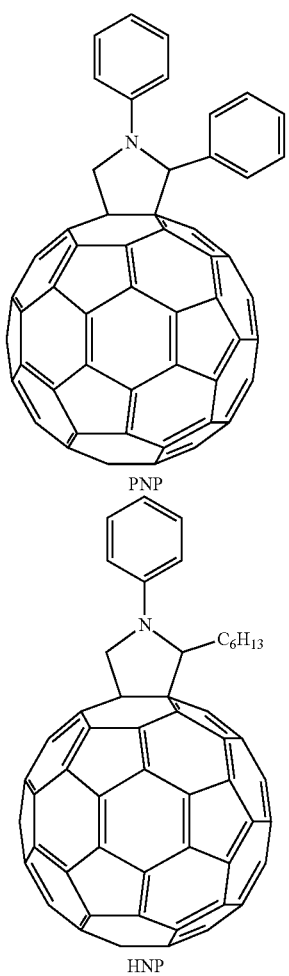

PNP

HNP

The term "multi-adduct product" in the Examples refers to a by-product compound that has two or more substituted pyrrolidine rings (the pyrrolidine ring shown in each structural formula) on the fullerene ring.

Example 1: Separation and Purification of PNP 0.1 g of a reaction mixture (starting material: $C_{60}$ 12%, target product: PNP, 75%, multi-adduct product 11%; the percentages of these materials are an area ratio of the HPLC peak) was dissolved in 5 mL of toluene, and the solution was added dropwise from above to a column tube packed with 10 g activated clay (Activated Clay, trade name, Wako Pure Chemical Industries, Ltd.) to allow the reaction mixture to adsorb to the activated clay. 300 mL of toluene was then passed through the column, thereby eluting the adsorption component from the column (treatment time: 1 hour). The following table illustrates the results of HPLC analysis of the fractions that contain the target product.

TABLE 1

| RT | HPLC Peak Area | Area Ratio of HPLC Peak |
| --- | --- | --- |
| 3.95 | 28759 | 0.751 |
| 5.50 | 3787304 | 98.938 |
| 8.46 | 11911 | 0.311 |

The target product fraction was confirmed to have an HPLC purity of 99.3%. The recovery percentage of the obtained target product calculated from the area ratio of HPLC peak before separation was 89%.

Example 2: Separation and Purification of HNP 0.1 g of the reaction mixture (starting material: $C_{60}$ 35%, target product: HNP 44%, and multi-adduct product: 21%; the percentages of these materials are an area ratio of the HPLC peak) was dissolved in 5 mL of toluene and added dropwise from above to a column tube packed with 10 g of activated clay (Activated Clay; trade name, Wako Pure Chemical Industries, Ltd.) to allow the reaction mixture to adsorb to the activated clay. 300 mL of a mixture solvent (toluene:methanol=95:5) was passed through the column, thereby eluting the adsorption component from the column (treatment time: 1 hour). The fractions were each analyzed by HPLC, and the target product fraction was confirmed to have a purity of 99.1%. The recovery percentage of the obtained target product was calculated from the area ratio of HPLC peak before separation, and confirmed to be 86%.

Tests shown in Comparative Example 1, Comparative Example 2, Example 3, and Comparative Example 4 were performed in the same manner as in Example 1 except that the solid phase and the liquid phase shown in Table 3 were used. The following table illustrates the results of HPLC analysis of the fractions containing the target product.

TABLE 2

| RT | HPLC Peak Area | Area Ratio of HPLC Peak |
| --- | --- | --- |
| 5.50 | 1462976 | 99.917 |
| 8.42 | 1217 | 0.083 |

Table 3 summarizes the results together with the results of Examples 1 and 2. The test in which Galleon Earth NFX (trade name, Mizusawa Industrial Chemicals, Ltd.) was used as activated clay instead of Activated Clay (trade name, Wako Pure Chemical Industries, Ltd.) also showed excellent results.

TABLE 3

| Target Product | Solid Phase Liquid Phase | Separation Efficiency Recovery Percentage | Purity After Treatment | Treatment Time | Amount of Solvent |
| --- | --- | --- | --- | --- | --- |
| Example 1 PNP | Activated Clay Toluene | 89% | 99.3% | 1 Hour | 0.3 L |
| Example 2 HNP | Activated Clay Toluene-Ethanol 95:5 | 86% | 99.1% | 1 Hour | 0.3 L |
| Comparative Example 1 PNP | Silica Gel Chromatography Hexane:Toluene | 55% | 99.3% | 6 Hours | 4 L |

TABLE 3-continued

| Target Product | Solid Phase Liquid Phase | Separation Efficiency Recovery Percentage | Purity After Treatment | Treatment Time | Amount of Solvent |
|---|---|---|---|---|---|
| Comparative Example 2 PNP | (1000:0 -> 0:100, Linear gradient) Celite = Diatomaceous Earth Hexane:Toluene 10:1 | 90% | Not Separated | | 1 L |
| Comparative Example 3 PNP | Cation Exchange Resin Hexane:Toluene 10:1 | 85% | Note Separated | 1 Hour | 1 L |

Example 3: Recovery of Unreacted $C_{60}$ Fullerene 1

10 L of a liquid of the reaction product mixture (in toluene) obtained in the same manner as in Example 2 was concentrated to 2 L, and 40 g of ethyl benzenesulfonic acid was added thereto, followed by stirring. 2 L of hexane was further added, and the mixture was stirred. The precipitate (sulfonate of HNP) was filtered through a 150 mesh, and washed with toluene and hexane (toluene/hexane=1/1). The solids were transferred to a 2-L beaker, and 300 mL of methanol was added thereto, followed by stirring and filtration three times each. The resulting solids were dried, thereby recovering a crude product of $C_{60}$. Crude Product Yield: 4.46 g, Purity: 65.6% (2.8% of $C_{60}$ was Contained)

Example 4: Recovery of Unreacted $C_{60}$ Fullerene 2

10 L of a liquid of the reaction product mixture (in toluene) obtained in the same manner as in Example 2 was concentrated under reduced pressure to 2 L, and 50 g of ethyl benzenesulfonic acid was added thereto, followed by stirring. 2 L of hexane was further added, and the mixture was stirred. This liquid was filtered through a 150 mesh. The obtained solids were washed with a solvent (hexane/toluene=1/1), and transferred to another container. 300 mL of methanol was added thereto, and stirring and filtration were performed three times each. The resulting solids were dried, thereby recovering a crude product of $C_{60}$.
Yield: 5.54 g (a crude product containing 2.7% of $C_{60}$)

Separately, the filtrate was dried and solidified under reduced pressure, thereby obtaining a recovered fullerene with a purity of 71%.
Yield: 4.12 g Example 5: Purification of Fullerene Derivative HNP Purification by Column Chromatography 1300 g of activated clay was formed into slurry by using toluene (containing 2% THF), and a column (10-cm diameter×60 cm) was packed with the slurry to a height of 30 cm. Separately, 4 g of the crude product was dissolved with heating in 1 L of toluene, and 80 g of activated clay was added thereto, followed by drying and solidifying them together under reduced pressure, thereby preparing a powder. This powder was then placed on the activated clay in the column. Toluene (containing 2% THF) was passed through the column at a flow rate of 7 to 9 mL while pressure was applied. A solution of the fullerene was first eluted, and HNP and its polysubstituted product were sequentially eluted. Fractions (about 100 mL each) of the eluates were taken, and the purity of HNP was confirmed by HPLC. The fractions with a purity of 99% or more were combined, and dried and solidified under reduced pressure. Its prior or post fractions with a purity of 90 to 99% were combined and purified again by column chromatography. This test was performed twice. The following table illustrates the results.

TABLE 4

| | First Time | | | | |
|---|---|---|---|---|---|
| Fraction No. | Amount of Liquid ml | Drying and Solidification g | Polysubstituted Product 3 to 4 minutes | HNP 4.8 minutes | C60 7.5 minutes |
| 1 | 100 | | 5.8 | 93.4 | 0.6 |
| 2 | 100 | 0.54 | 4.1 | 93.3 | 2.6 |
| 3 | 75 | | 3.3 | 96.5 | 0.2 |
| 4 | 75 | | 1.4 | 98.6 | 0.0 |
| 5 | 130 | 0.44 | 0.9 | 99.1 | 0.0 |
| 6 | 70 | 0.40 | 0.5 | 99.5 | 0.0 |
| 7 | 70 | | 0.7 | 99.3 | 0.0 |
| 8 | 45 | | 0.7 | 99.4 | 0.0 |
| 9 | 100 | 0.39 | 2.1 | 97.9 | 0.0 |
| 10 | 80 | | 4.2 | 94.4 | 0.0 |
| 11 | 150 | 0.57 | 11.1 | 88.8 | 0.0 |
| 12 | 300 | | 33.7 | 65.1 | 0.4 |
| 13 | 150 | 0.28 | 76.2 | 22.2 | 0.8 |
| Total | 1,445 | 2.62 | | | |

TABLE 4-continued

| | | Second Time | | | |
|---|---|---|---|---|---|
| Fraction No | Amount of Liquid ml | Drying and Solidification g | Polysubstituted Product 3 to 4 minutes | HNP 4.8 minutes | C60 7.5 minutes |
| 1 | 110 | — | 23.2 | 76.8 | — |
| 2 | 60 | 0.21 | 5.1 | 93.1 | 1.8 |
| 3 | 45 | | 4.0 | 94.6 | 0.3 |
| 4 | 30 | | 2.7 | 96.5 | 0.8 |
| 5 | 50 | | 2.5 | 97.9 | 0.6 |
| 6 | 30 | | 1.4 | 98.2 | 0.4 |
| 7 | 50 | | 1.4 | 98.3 | 0.3 |
| 8 | 70 | | 1.2 | 98.6 | 0.2 |
| 9 | 100 | 0.83 | 0.8 | 99.2 | 0.0 |
| 10 | 90 | | 0.7 | 99.3 | 0.0 |
| 11 | 130 | | 0.8 | 99.2 | 0.0 |
| 12 | 80 | | 0.6 | 99.5 | 0.0 |
| 13 | 65 | | 0.8 | 99.2 | 0.0 |
| 14 | 100 | | 0.8 | 99.2 | 0.0 |
| 15 | 70 | 0.70 | 2.1 | 97.9 | 0.0 |
| 16 | 90 | | 4.2 | 95.8 | 0.0 |
| 17 | 100 | | 11.5 | 88.4 | 0.0 |
| 18 | 100 | | | | |
| Total | 1,370 | 1.74 | | | |

Example 6: Study into Developing Solvents for Purification of Fullerene Derivatives PNP and HNP Suitable developing solvents for purification of fullerene derivatives PNP and HNP were studied. The following table illustrates the results. Adsorption to activated clay differed between PNP and HNP. When toluene alone was used for the mobile phase, unlike PNP, target HNP was not eluted and remained adsorbed to the activated clay. The optimum ratio was determined by mixing various polar solvents, and toluene containing 2% of HF was confirmed to be most suitable.

Selection of Mobile Phase: Tol.: toluene; R: $CH_3$—, $CH_3$—$CH_2$—)

TABLE 5

| | PNP | | | HNP | | |
|---|---|---|---|---|---|---|
| Order of Elution | C60 | PNP | Polysubstituted Product | C60 | HNP | Polysubstituted Product |
| Tol. Alone | Eluted at the tip | Neatly Separated | Remained adsorbed and not eluted | Eluted at the tip | | Remained adsorbed and not eluted |
| Tol./Hexane | — | — | — | Eluted at the tip | | Remained adsorbed and not eluted |
| Tol./R—OH | — | — | — | Eluted together at the tip | | |
| Tol./THF | — | — | — | Eluted together at the tip | | |
| Tol./THF | — | — | — | Separated and eluted in the following order: C60->HNP->Polysubstituted Product | | |

The invention claimed is:
1. A method for purifying a fullerene derivative represented by formula (1):

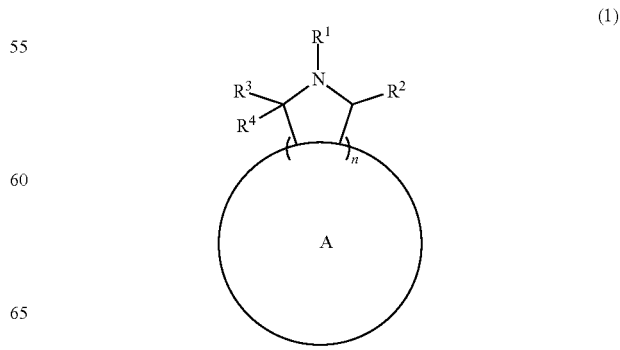

(1)

wherein
- R¹ represents an aryl group,
- R² represents an aryl group,
- R³ represents a hydrogen atom,
- R⁴ represents a hydrogen atom,
- ring A represents a fullerene ring,
- n represents a number of 1 or more, and
- when n is 2 or more, in one or more pairs of monocyclic moieties represented by the following partial formula:

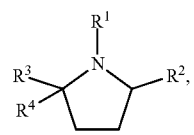

one substituent selected from the group consisting of R², R³, and R⁴ of one of the two monocyclic moieties is connected with one substituent selected from the group consisting of R², R³, and R⁴ of the other of the two monocyclic moieties to form a tricyclic moiety, the method comprising step 1 of contacting a composition containing the fullerene derivative represented by formula (1) as a target product for purification and one or more impure fullerene compounds with an aluminum-containing inorganic porous adsorbent, wherein the aluminum-containing inorganic porous adsorbent is activated clay, and wherein the one or more impure fullerene compounds include at least one member selected from the group consisting of a fullerene derivative (i), an oxide of the fullerene derivative (i), a fullerene derivative (lm) represented by formula (1), an oxide of the fullerene derivative (lm) represented by formula (1), a fullerene $C_{60}$, and an oxide of the fullerene $C_{60}$, wherein the fullerene derivative (i) is represented by formula (i):

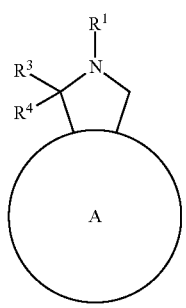

wherein
- R¹ represents an organic group,
- R³ represents a hydrogen atom,
- R⁴ represents a hydrogen atom, and
- ring A represents a fullerene ring, and wherein the fullerene derivative (lm) is represented by formula (1):

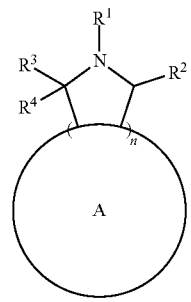

wherein
- R¹ represents an organic group,
- R² represents an organic group,
- R³ represents a hydrogen atom or an organic group,
- R⁴ represents a hydrogen atom or an organic group,
- ring A represents a fullerene ring, and
- n is a number of 2 or more.

2. The purification method according to claim 1, wherein, in the fullerene derivative represented by formula (1),
- ring A is a $C_{60}$ fullerene,
- R² is an aryl group that is substituted with at least one alkyl group.

3. The purification method according to claim 1, wherein, in the fullerene derivative represented by formula (1), n is 1.

4. The purification method according to claim 1, wherein the aluminum-containing inorganic porous adsorbent has a median size of 50 to 500 μm.

5. The purification method according to claim 1, wherein step 1 is a step of introducing the composition containing the fullerene derivative represented by formula (1), which is a target product for purification, and the one or more impure fullerene compounds into a column containing activated clay, which is a solid phase; and the method further comprises step 2 of allowing a solvent, which is a liquid phase, to flow through the column having the composition introduced to elute the fullerene derivative represented by formula (1) from the column.

6. The purification method according to claim 5, wherein the flow rate of the fullerene derivative represented by formula (1) per column cross-section area of 0.002 m² is 0.001 to 50 g/min.

7. The purification method according to claim 5, wherein the flow rate of the solvent per column cross-section area of 0.002 m² is 0.5 to 50 L/hr.

8. The purification method according to claim 5, wherein the amount of the solvent used per column cross-section area of 0.002 m² is 0.5 to 100 L.

9. The purification method according to claim 5, wherein the ratio of the amount of the solvent used to the amount of the introduced fullerene derivative represented by formula (1) is 0.1 to 10 L/g.

10. The purification method according to claim 5, wherein the column has a length of 0.1 to 5 m.

11. The purification method according to claim 1, wherein the temperature of treatment is 0° C. to 100° C.

12. The purification method according to claim 5, wherein the solvent is selected from the group consisting of chlorine solvents, hydrocarbon solvents, chlorinated aromatic solvents, alcohol solvents, ether solvents, ketone solvents, non-polar solvents, low-polar solvents, and combinations thereof.

13. The purification method according to claim 5, wherein the solvent is selected from the group consisting of carbon disulfide, chloroform, dichloroethane, toluene, xylene, chlorobenzene, dichlorobenzene, ethanol, methanol, tetrahydrofuran, acetone, and combinations thereof.

14. The purification method according to claim 5, wherein the treatment time is 0.1 to 72 hours.

15. The purification method according to claim 5, wherein the treatment time is 0.5 to 5 hours.

* * * * *